United States Patent
Bae et al.

(10) Patent No.: US 9,307,937 B2
(45) Date of Patent: Apr. 12, 2016

(54) APPARATUS AND METHOD FOR MEASURING BIOMEDICAL DATA USING ALGORITHM FOR IMPROVING REPRODUCIBILITY

(75) Inventors: Byeong-Woo Bae, Anyang (KR); Sung-Dong Lee, Anyang (KR); Byung-Hoon Kho, Seongnam (KR); Ji-Eon Ryu, Anyang (KR); Jin-Kyeong Kim, Gunpo (KR); Hyou-Arm Joung, Uiwang (KR); Yooh-Hee Lee, Seoul (KR)

(73) Assignee: INFOPIA CO., LTD. (KR)

( * ) Notice: Subject to any disclaimer, the term of this patent is extended or adjusted under 35 U.S.C. 154(b) by 854 days.

(21) Appl. No.: 12/722,110

(22) Filed: Mar. 11, 2010

(65) Prior Publication Data
US 2010/0311090 A1    Dec. 9, 2010

(30) Foreign Application Priority Data
Jun. 4, 2009    (KR) .................. 10-2009-0049645

(51) Int. Cl.
| | |
|---|---|
| G01N 33/50 | (2006.01) |
| A61B 5/145 | (2006.01) |
| G06F 19/00 | (2011.01) |
| A61B 5/1455 | (2006.01) |
| G01N 33/487 | (2006.01) |
| G06G 7/58 | (2006.01) |

(52) U.S. Cl.
CPC ......... *A61B 5/14546* (2013.01); *A61B 5/1455* (2013.01); *G01N 33/48785* (2013.01); *G06F 19/30* (2013.01); *G06F 19/3406* (2013.01); *G06F 19/34* (2013.01)

(58) Field of Classification Search
CPC ................................ G06F 19/30; G06F 19/34
See application file for complete search history.

(56) References Cited

U.S. PATENT DOCUMENTS

| | | | |
|---|---|---|---|
| 5,885,839 A | 3/1999 | Lingane et al. | |
| 6,193,873 B1 | 2/2001 | Ohara et al. | |
| 6,268,162 B1 | 7/2001 | Phillips et al. | |
| 6,541,266 B2 | 4/2003 | Modzelewski et al. | |
| 6,844,149 B2 * | 1/2005 | Goldman | 435/4 |
| 2002/0146835 A1 | 10/2002 | Modzelewski et al. | |
| 2004/0078149 A1 | 4/2004 | Matzinger | |

FOREIGN PATENT DOCUMENTS

| | | |
|---|---|---|
| CN | 1508534 A | 6/2004 |
| CN | 1668916 A | 9/2005 |
| CN | 1715898 A | 1/2006 |
| CN | 1886651 | 12/2006 |
| CN | 101236161 A | 8/2008 |
| EP | 0974303 A1 | 1/2000 |
| JP | 2004144750 A | 5/2004 |
| KR | 1020040028437 A | 4/2004 |
| KR | 1020040034545 A | 4/2004 |
| KR | 1020090033065 A | 4/2009 |
| WO | 2009041782 A2 | 4/2009 |

OTHER PUBLICATIONS

International Search Report; PCT/KR2010/002407; Nov. 26, 2010.
Chinese Office Action—CN Application No. 100004 dated Dec. 4, 2013, cited U.S. Pat. No. 5,885,839.
Chinese Office Action—CN Application No. 100004 dated Jun. 26, 2013, cited CN1886651 and CN1508534.
Extended European Search Report for Application No. 10783518.3; Dated: Feb. 3, 2014.
Japanese Office Action—JP Application No. 20120513855 dated May 24, 2013, cited JP2004144750A.

* cited by examiner

*Primary Examiner* — Eric S Dejong
(74) *Attorney, Agent, or Firm* — Cantor Colburn LLP

(57) ABSTRACT

Disclosed herein is a method and apparatus for measuring biomedical data. The method of measuring biomedical data using a biochemical reaction includes determining reaction termination time at which the biochemical reaction has been stabilized based on an average variation in a predetermined period in an early stage of measurement, and obtaining a final measured value by adding a correction value to a value measured at the determined reaction termination time.

4 Claims, 4 Drawing Sheets

APPARATUS AND METHOD FOR MEASURING BIOMEDICAL DATA USING ALGORITHM FOR IMPROVING REPRODUCIBILITY

BACKGROUND OF THE INVENTION

1. Field of the Invention

The present invention relates to the measurement of biomedical data.

2. Description of the Related Art

Dry chemistry refers to the use of strips impregnated with a dry enzyme to which the specimen is added. This assessment method focuses on quantitative analysis of the chemical reactions by computer analyzers.

This assessment method causes the differences between measurement results obtained using the same specimen due to environmental factors, such as the amount of specimen, the specimen injection method and temperature, besides chemical and biological factors. In particular, there is a strong possibility that an apparatus for measuring biomedical data at home other than a laboratory causes great differences. Since the differences between measurement results cast doubt on the accuracy of the measurement results, a method of ensuring the reproducibility of measurement results is required.

SUMMARY OF THE INVENTION

Accordingly, the present invention has been made keeping in mind the above problems occurring in the prior art, and an object of the present invention is to provide an apparatus and method for measuring biomedical data using an algorithm for improving reproducibility which improves reproducibility by reducing the differences between measurement results, thereby ensuring the reliability of the measurement results.

According to one aspect of the present invention, there is provided a method of measuring biomedical data in an apparatus for measuring biomedical data using a biochemical reaction, including determining reaction termination time at which the biochemical reaction has been stabilized based on an average variation in a predetermined period in an early stage of measurement; and obtaining a final measured value by adding a correction value to a value measured at the determined reaction termination time.

According to another aspect of the present invention, there is provided an apparatus for receiving a measurement strip and measuring biomedical data using the measurement strip, including one or more detection units arranged within an strip reception area on one plane; a correction data generation unit for generating correction data based on data detected by the detection unit; a reaction termination time determination unit for determining reaction termination time based on the data detected by the detection unit; a biomedical data measurement unit for measuring biomedical data based on the data detected by the detection unit at the determined reaction termination time and the generated correction data; and an output unit for outputting the biomedical data to an outside.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, preferred embodiments of the present invention will be described in detail with reference to the accompanying drawings so that they can be readily implemented by those skilled in the art.

Figure 1:
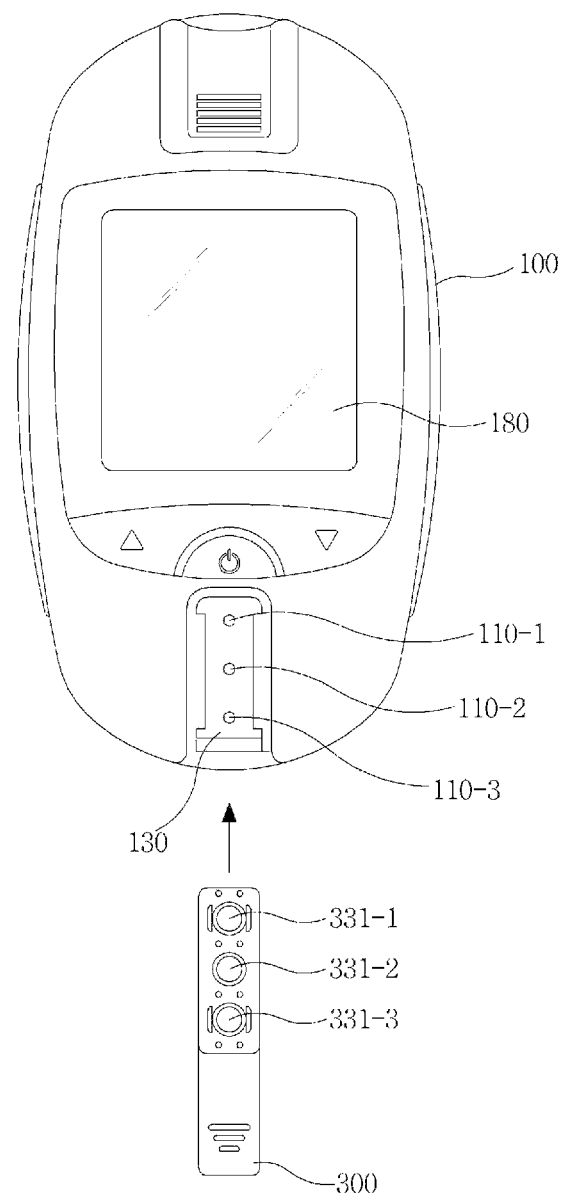
FIG. 1 is a schematic diagram showing an apparatus for measuring biomedical data and a measurement strip.

FIG. 1 is a schematic diagram showing an apparatus for measuring biomedical data and a measurement strip according to an embodiment of the present invention. Referring to FIG. 1, the measurement strip 300 includes a support part 330 which includes a plurality of reactive portions (e.g., 331-1, 331-2, and 331-3) capable of measuring biomedical data, such as the neutral lipid of blood and the amount of cholesterol. The support part 330 including the reactive portions has target data varying depending on position. Projections are formed on the top of the measurement strip 300 so that the measurement strip 300 can be inserted into a strip reception area 130 with the projections of the measurement strip 300 engaged with the depressions of the strip reception area 130 and with the measurement strip 300 easily fastened within the strip reception area 130. The apparatus for measuring biomedical data 100 includes a power button, the strip reception area 130, and a display unit 180. The apparatus for measuring biomedical data 100 has a structure in which the depressions are formed in the periphery of the strip reception area 130 so that the measurement strip 300 can be easily inserted and fastened thereinto. The strip reception area 130 includes a plurality of detection units 110 (e.g., 110-1, 110-2, and 110-3) which are formed along the central portion of the strip reception area 130 and which are spaced apart from each other. The plurality of detection units 110 correspond to the reactive portions of the measurement strip 300, respectively. Part or all of the detection units are activated depending on the type of measurement, and detect reactive areas including corresponding reactive portions.

According to the embodiment of the present invention, biomedical data is measured based on the reflectance of the reactive portion of the measurement strip inserted into the apparatus 100 for measuring biomedical data, which is detected by the plurality of detection units 110. In greater detail, when blood is provided from above a region including the reactive portion of the strip, a chemical reaction occurs between the enzyme of the reactive portion and the provided blood. At this time, the color of the reactive portion which is white at the beginning is changed to a color other than white, the reflectance of the discolored reactive portion is detected using the plurality of detection units 110 and then biomedical data is created based on the reflectance using a biomedical data measurement unit.

Figure 2:
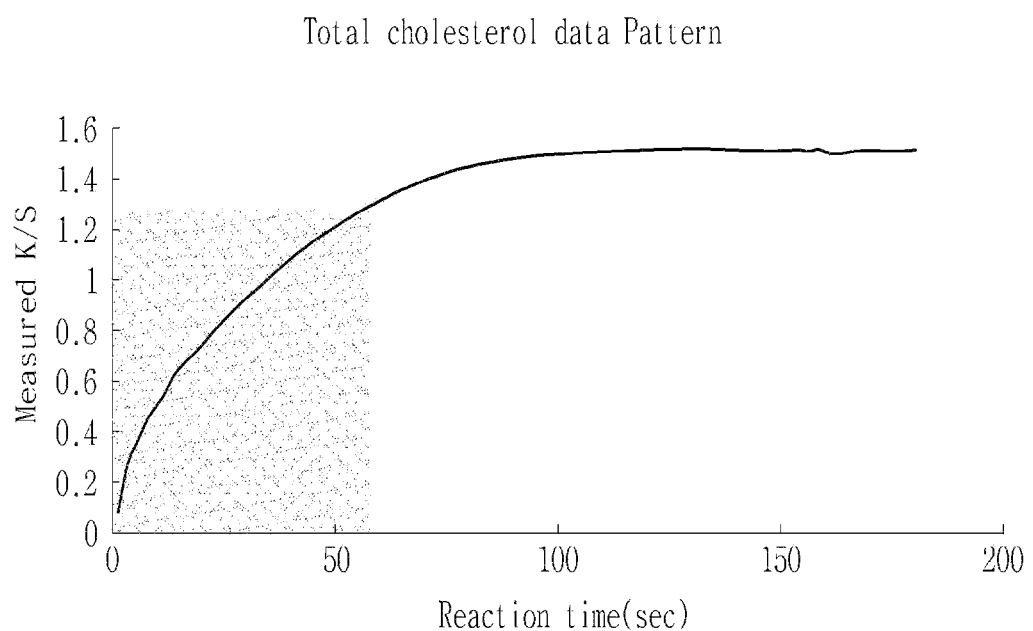
FIG. 2 is a graph showing the reaction of total cholesterol according to an embodiment of the present invention.

FIG. 2 is a graph showing the characteristics of a chemical reaction between total cholesterol and enzyme over time according to an embodiment of the present invention. In FIG. 2, the horizontal axis of the graph represents reaction time, and the vertical axis thereof represents a value obtained by measuring the reflectance of the reactive portion (hereinafter referred to as a "K/S value"). From FIG. 2, it can be seen that a chemical reaction between total cholesterol and the enzyme actively occurs for the first 50 minutes, that is, an active interval, and a chemical reaction barely occurs thereafter.

Here, an average K/S variation in a predetermined interval in the first stage of a reaction is referred to as an "A-value." The start and end of the interval in which an A-value is obtained may vary depending on the measuring type. According to an embodiment, when total cholesterol is measured, an A-value is an average K/S variation in a period between 15 minutes and 30 minutes, and is determined using the following Equation 1:

$$A\text{-value} = \frac{K/S_{(30\ sec)} - K/S_{(15\ sec)}}{(30-15)} \quad (1)$$

According to an embodiment of the present invention, reaction termination time is determined using an A-value. The reaction termination time is determined using the following Equation 2:

$$((A\text{-value}) \times 0.3) \geq \frac{K/S_{((a+5)\ sec)} - K/S_{(a\ sec)}}{5} \quad (2)$$

According to Equation 2, when the average variation for five seconds starting from an arbitrary second 'a' is equal to or less than (A-value*0.3), a reaction is considered to be terminated, and then the second 'a' is determined to be reaction termination time. 0.3 by which the A-value is multiplied is a determination constant which is used to determine measurement termination time. The determination constant is determined depending on the type of measurement. According to an embodiment, the determination constant is determined between 0.001 and 0.5. In the case of the measurement of total cholesterol, the determination constant is experimentally determined to be 0.3.

In general, temperature significantly influences reaction rate. When temperature increases, an enzyme reaction is activated, so that reaction rate is increased. When temperature decreases, an enzyme reaction is inactivated, so that reaction rate is decreased. When the reaction rate is fast, reaction termination time is reached rapidly. In contrast, when the reaction rate is slow, reaction termination time is reached slowly. Since an A-value is an average variation in the early stage of a reaction, this is an index indicative of the reaction rate of an enzyme under specific conditions. Accordingly, the determination of reaction termination time using an A-value in Equation 2 is the reasonable determination of measuring time which takes into consideration reaction conditions such as temperature.

Figure 3:
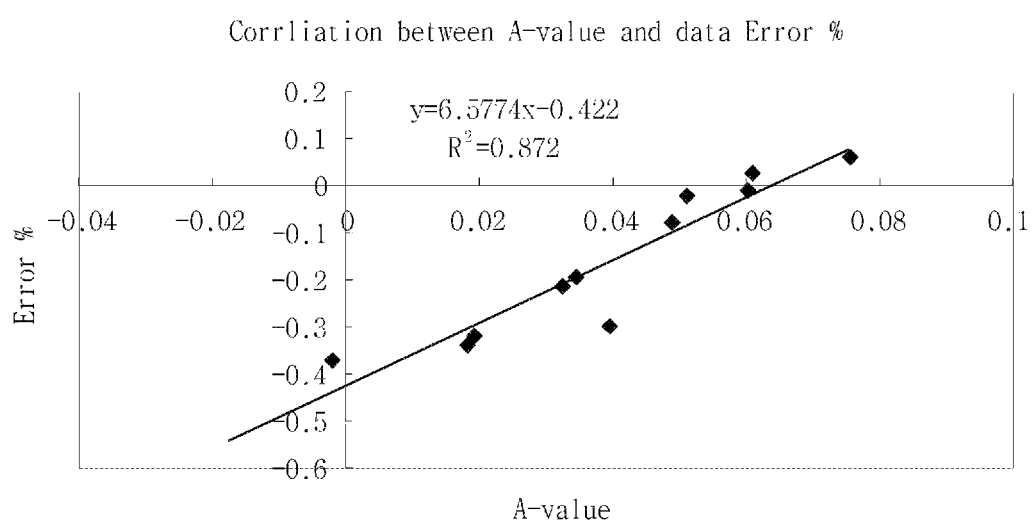
FIG. 3 is a graph showing the correlation between average variation and data error rate for the same blood in a specific interval in the early stage of a reaction according to an embodiment of the present invention.

FIG. 3 is a graph showing the correlation between average variation and data error rate for the same blood in a specific interval in the early stage of a reaction according to an embodiment of the present invention. According to an embodiment, an experiment for measuring total cholesterol using the same blood is repeated, and a graph plotting A-values versus the differences between the average values of measured data and measured values. From this graph, it can be seen that the difference occurring at the reaction termination time has a positive correlation with the A-value. This means that a measured result value can be corrected, and correction using a result value in the early stage of a reaction is effective. According to an embodiment, a final measurement value may be determined using the following Equation 3:

Final measured value=$K/S$ at reaction termination time$-(K/S_{(30\ sec)} - K/S_{(15\ sec)})$ (3)

According to Equation 3, a final measured value is a value which is obtained by adding correction data to a K/S value at reaction termination time. The correction data corresponds to the negative value of the numerator of Equation 1, and is determined depending on the measurement type. For example, when total cholesterol is measured, the correction data corresponds to the difference in the K/S value between 15 seconds and 30 seconds, as indicated by Equation 3. Reaction conditions such as temperature and the amount of injection of specimen influence reaction rate as described above, and this influence is exhibited in the form of a variation in the K/S value in the early stage of a reaction. Furthermore, the variation in the K/S value in the early stage of a reaction significantly influences the overall reaction. Therefore, when a final measured value is calculated using the fact, the differences related to the same specimen can be effectively reduced, and reproducibility can be ensured.

Figure 4:
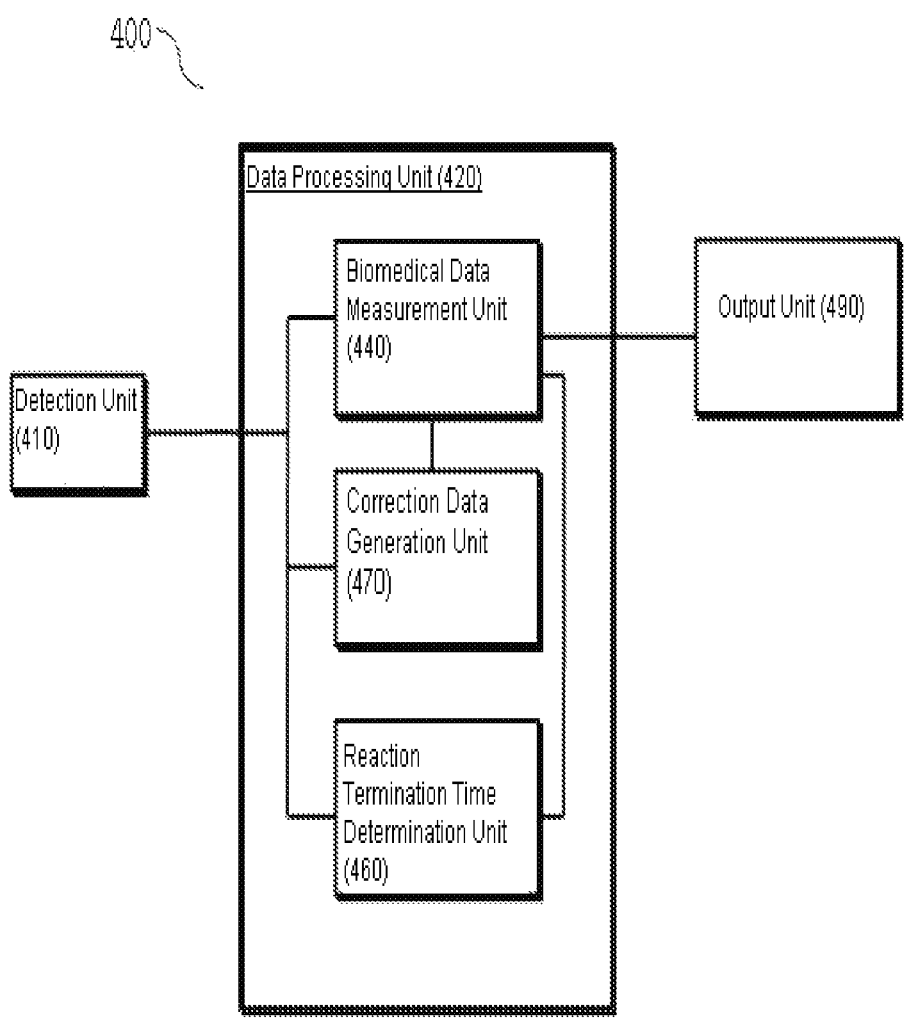
FIG. 4 is a schematic block diagram showing an apparatus for measuring biomedical data according to an embodiment of the present invention.

FIG. 4 is a schematic block diagram showing an apparatus for measuring biomedical data according to an embodiment of the present invention. Referring to FIG. 4, the apparatus for measuring biomedical data 200 includes one or more detection units 410, a data processing unit 420, and an output unit 480. The data processing unit 420 includes a biomedical data measurement unit 440, a reaction termination time determination unit 460, and a biomedical data correction unit 470.

In greater detail, the one or more detection units 410 detect respective areas of the strip corresponding to the detection units. The one or more detection units 410 are implemented to measure the reflectance of the reactive areas of the measurement strip corresponding to the detection units. Each of the detection units 410 may be configured to include a light-emitting unit and a light-receiving unit. The light-emitting unit of each detection unit may include a Light-Emitting Diode (LED) for generating light and a drive circuit, while the light-receiving unit of the detection unit may include a photodiode for absorbing light and an analog-to-digital converter. The detection unit receives light reflected from the corresponding reactive area of the measurement strip, converts the amount of received light into a K/S value, and sends the resulting value to the biomedical data measurement unit 440, the correction data generation unit 470 and the reaction termination time determination unit 460.

The reaction termination time determination unit 460 determines reaction termination time based on results detected by the detection unit. According to an embodiment, K/S values detected by the detection unit are successively input to the reaction termination time determination unit, and the reaction termination time determination unit 460 determines the average variation in a period from 15 seconds to 30 seconds in the early stage of a reaction to be the A-value. Furthermore, the reaction termination time determination unit 460 determines the reaction termination time using the above-described Equation 2. When the average variation for five seconds starting from an arbitrary second 'a' is equal to or less than (A-value*0.3), a reaction is considered to be terminated, and then the second 'a' is determined to be the reaction termination time. 0.3 by which the A-value is multiplied is a determination constant which is used to determine the measurement termination time. The determination constant is determined depending on the type of measurement. As an example, in the case of the measurement of total cholesterol, the determination constant is experimentally determined to be 0.3.

The correction data generation unit 470 generates correction data based on detection results acquired by the detection unit. According to an embodiment, the correction data generation unit 470 generates the negative value of the numerator of the above-described Equation 1 as correction data. The interval during which correction data is generated is determined depending on the type of measurement. As an example, when total cholesterol is measured, correction data corresponds to the difference in the K/S value in a period between 15 seconds and 30 seconds, as indicated by Equation 3.

The biomedical data measurement unit 440 measures biomedical data based on the data detected at the reaction termination time by the detection unit and the correction data. According to an embodiment, the biometric data measuring unit 440 determines a final measured value using Equation 3. In detail, the final measured value is determined by adding the K/S value detected at the time when the average variation is equal to or less than (A-value*0.3) by the detection unit and the correction data, that is, the negative value of the difference in the K/S value in a period between 15 seconds and 30 seconds, generated by the correction data determination unit 470. As described above, the correction data may vary depending on the type of measurement. The final measured value is converted into biomedical data in conformity with the type of measurement.

The measured biomedical data is output to the outside through the output unit 480. According to an embodiment, the output unit 480 may be a liquid crystal display or a 7-segment display. According to another embodiment, the output unit 480 may be a voice synthesis and output unit which outputs a measured value in the form of voice. According to yet another embodiment, the output unit 480 may be an interface, such as a Universal Serial Bus (USB), which outputs a measured value to an external device, such as a mobile phone.

The method of measuring biomedical data according to the present invention is configured to determine reasonable reaction termination time and a correction value based on reaction rate, thereby improving reproducibility and data reliability by reducing the differences between measurement results.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of measuring biomedical data using an apparatus for measuring biomedical data, comprising:
   inserting a measurement strip into the apparatus for measuring the biomedical data;
   applying blood to a reactive portion of the measurement strip on which enzyme material for measuring cholesterol is provided;
   detecting color change of the reactive portion of measurement strip in a predetermined period of measurement as a result of the biochemical reaction between the blood and the enzyme material on the reactive portion;
   determining reflectance of the reactive portion of the measurement strip in the predetermined period of measurement based on the color change;
   detecting a point of time at which a current average variation is a value which is equal to or less than a value obtained by multiplying the average variation of the dertermined reflectance in the predetermined period of measurement by a determination constant;
   determining reaction termination time according to the point of time;
   generating a correction value by calculating a difference between a measured value at a start of the predetermined period of measurement and a measured value at an end of the predetermined period of measurement;
   obtaining a final measured value by adding the correction value to a value of the reflectance measured at the determined reaction termination time; and
   converting the final measured value into the biomedical data.

2. The method set forth in claim 1, wherein the biochemical reaction is an enzyme reaction.

3. The method as set forth in claim 1, wherein the determination constant is in a range from 0.001 to 0.5.

4. The method as set forth in claim 1, wherein the predetermined period of measurement is determined depending on the type of measurement.

* * * * *